(12) United States Patent
Fukuda et al.

(10) Patent No.: US 7,326,827 B2
(45) Date of Patent: Feb. 5, 2008

(54) SODIUM/PROTON ANTIPORTER GENE

(75) Inventors: Atsunori Fukuda, Ibaraki (JP); Yoshiyuki Tanaka, Ibaraki (JP)

(73) Assignee: National Institute of Agrobiological Sciences (JP)

( * ) Notice: Subject to any disclaimer, the term of this patent is extended or adjusted under 35 U.S.C. 154(b) by 0 days.

(21) Appl. No.: 10/944,174

(22) Filed: Sep. 16, 2004

(65) Prior Publication Data

US 2005/0032112 A1 Feb. 10, 2005

Related U.S. Application Data

(60) Division of application No. 09/888,035, filed on Jun. 22, 2001, now Pat. No. 6,861,574, which is a continuation-in-part of application No. PCT/JP99/07224, filed on Dec. 22, 1999.

(30) Foreign Application Priority Data

Dec. 22, 1998 (JP) ................. 10/365604

(51) Int. Cl.
C12N 15/82 (2006.01)
C12N 15/29 (2006.01)
C12N 5/10 (2006.01)
A01H 5/00 (2006.01)

(52) U.S. Cl. .............. 800/289; 800/298; 800/320; 800/320.2; 435/419; 435/252.3; 536/23.6; 536/24.3

(58) Field of Classification Search ........... 800/289, 800/298, 320
See application file for complete search history.

(56) References Cited

U.S. PATENT DOCUMENTS

| | | | |
|---|---|---|---|
| 4,616,100 A | 10/1986 | McHughen et al. | |
| 5,272,085 A | 12/1993 | Young et al. | |
| 5,346,815 A | 9/1994 | Krulwich et al. | |
| 5,441,875 A | 8/1995 | Hediger | |
| 5,563,246 A | 10/1996 | Krulwich et al. | |
| 5,563,324 A | 10/1996 | Tarczynski et al. | |
| 5,639,950 A | 6/1997 | Verma et al. | |
| 5,689,039 A | 11/1997 | Becker et al. | |
| 5,750,848 A | 5/1998 | Kruger et al. | |
| 5,780,709 A | 7/1998 | Adams et al. | |
| 5,859,337 A | 1/1999 | Gasser et al. | |
| 6,861,574 B2 * | 3/2005 | Fukuda et al. ............. | 800/289 |
| 2003/0046729 A1 | 3/2003 | Blumwald et al. | |
| 2005/0028235 A1 | 2/2005 | Zhang et al. | |
| 2005/0032112 A1 | 2/2005 | Fukuda et al. | |
| 2005/0034191 A1 | 2/2005 | Blumwald | |
| 2005/0144666 A1 | 6/2005 | Blumwald et al. | |
| 2005/0155105 A1 | 7/2005 | Blumwald et al. | |
| 2005/0204430 A1 | 9/2005 | Blumwald et al. | |
| 2006/0195948 A1 | 8/2006 | Blumwald et al. | |

FOREIGN PATENT DOCUMENTS

| | | |
|---|---|---|
| EP | 1 143 002 A1 | 10/2001 |
| JP | 2000-157287 A1 | 6/2000 |
| WO | WO 91/06651 A1 | 5/1991 |
| WO | WO 96/39020 A1 | 12/1996 |
| WO | WO 97/13843 A1 | 4/1997 |
| WO | WO 99/47679 A2 | 9/1999 |
| WO | WO 00/37644 A1 | 6/2000 |

OTHER PUBLICATIONS

Fukuda, A., et al. 1999. BBA 1446: 149-155.*
Gaxiola, R.A., et al. 1999. PNAS 96: 1480-1485.*
Rice Mutant Database reference sheet.*
Dante, M. et al. "The *A. thaliana* TM021B04" Database—Genbank accession No. AF007271, Unpublished 1997, Retrieved Jun. 12, 1997.
Sante-Maria, G. et al. "The *HAK1* Gene of Barley is a Member of a Large Gene Family and Encodes a High-Affinity Postassium Transporter" *The Plant Cell*, Dec. 1997, pp. 2281-2289, vol. 9 No. 12, American Society of Plant Physiologists, USA.
Al-Karaki, G. "Growth, water use efficiency, and sodium and potassium acquisition by tomato cultivars grown under salt stress" *J. Plant Nutrition*, 2000, 23:1-8.
Apse, M.P. "Identification of two putative sodium/proton antiports in *Arabidopsis*" Plant Membrane Biology Workshop, Aug. 1998, Cambridge, U.K., poster.
Apse, M.P. and Blumwald, E. "Engineering salt tolerance in plants" *Current Opin Biotechnology*, 2002, 13:146-150.
Apse, M.P. et al. "Cloning and characterization of a plant sodium/proton antiport" Annual Meeting of the American Society of Plant Physiologists, Jun. 1998 Madison, WI, abstract.
Apse, M.P. et al. "Cloning and Characterization of Plant Sodium/Proton Antiports" 11th International Workshop on Plant Membrane Biology Aug. 1998, Cambridge, U.K., abstract.
Apse, M.P. et al. "Salt tolerance conferred by overexpression of a vacuolar $Na^+/H^+$ antiport in *Arabidopsis*" *Science*, 1999, 285:1256-1258.
Barkla, B.J. et al. "The plant vacuolar $Na^+/H^+$ antiport" *Symp. Soc. Exp. Biol.*, 1994, 48:141-153.
Barkla, B.J. et al. "Tonoplast $Na^+/H^+$ antiport activity and its energization by the vacuolar $H^+$-ATPase in the halophytic plant *Mesembryanthemum crystallinum* L" *Plant Physiol.*, 1995, 109:549-556.
Blumwald, E. "Sodium transport and salt tolerance in plants" *Curr Opin Cell Biol*, 2000, 12:431-434.
Bohnert, H.J. and Jensen, R.G. "Strategies for engineering water-stress tolerance in plants" *Trends Biotechnology*, 1996, 14:89-97.
Borgese, F. et al. "Cloning and expression of a cAMP-activated $Na^+/H^+$ exchanger: Evidence that the cytoplasmic domain mediates hormonal regulation" *Proc. Natl. Acad. Sci. USA*, 1992, 89:6765-6769.

(Continued)

*Primary Examiner*—Maryam Monshipouri
*Assistant Examiner*—Marsha Tsay
(74) *Attorney, Agent, or Firm*—Saliwanchik, Lloyd & Saliwanchik

(57) ABSTRACT

The present inventors successfully cloned the rice $Na^+/H^+$ antiporter gene. It is possible to produce salt tolerant plants by using the isolated gene, or genes with equivalent functions.

12 Claims, 6 Drawing Sheets

OTHER PUBLICATIONS

Bork, P. "Powers and pitfalls in sequence analysis: The 70% hurdle" *Genome Res*, 2000, 10:398-400.

Bowie, J.U. et al. "Deciphering the message in protein sequences: Tolerance to amino acid substitutions" *Science*, 1990, 247:1306-1310.

Broun, P. et al. "Catalytic plasticity of fatty acid modification enzymes underlying chemical diversity of plant lipids" *Science*, 1998, 282:1315-1317.

Counillon, L. et al. "A Point Mutation of the $Na^+/H^+$ Exchanger Gene (NHE1) and Amplification of the Mutated Allele confer Amiloride Resistance upon Chronic Acidosis" *Proc. Natl. Acad. Sci. USA*, 1993, 90:4508-4512.

Cuartero, J. and Fernandez-Munoz, R. "Tomato and salinity" *Scientia Horticulturae*, 1999, 78:83-125.

Darley, C.P. et al. "ANA1 a $Na^+/H^+$ Antiporter From *Arabidopsis*?" 11th International Workshop on Plant Membrane Biology, Aug. 1998, Cambridge, U.K.

EMBL Database Accesssion No. AB021878, *Oryza sativa* (Japonica cultivar-group) OsNHX1 mRNA, complete cds 1999.

EMBL Database Accession No. AF007271, *Arabidopsis thaliana* BAC TM021B04, 1997.

EMBL Database Accession No. D49589, *Homo sapiens* DNA, alphoid Sau3A repetitive family, clone:I-3, 1995.

Fukuda, A. et al. "Molecular Cloning and Expression of the $Na^+/H^+$ Exchanger Gene in *Oryza sativa* " *Biochimica et Biophysica Acta*, 1999, 1446:149-155.

Fukuda, A. et al. "$Na^+/H^+$ Antiporter in Tonoplast Vesicles from Rice Roots" *Plant cell Phsyiol*, 1998, 39(2):196-201.

Fukuda, A. et al, "The functional analysis of the rice $Na^+/H^+$ antiporter gene," *Plant and Cell Physiology*, 2001, 42(Supplement):s210, presented at Symposia of Workshops of the 2001 Annual Meeting of the Japanese Society of Plant Physiologists; Fukuoka, Japan, Mar. 23-26, 2001, abstract.

Gaxiola, R.A. et al., "The *Arabidopsis thaliana* Proton Transporters, AtNhx1 and Avpl, Can Function in Cation Detoxification in Yeast" *Proc. Natl. Acad. USA*, 1999, 96:1480-1485.

GenBank Accession No. 3850064, Putative Na/H exchanger, 1998.
GenBank Accession No. 927695, *Saccharomyces cerevisiae*, 1997.
GenBank Accession No. AA660573, MtRHE *Medicago truncatula* cDNA 5', mRNA sequence, 2000.
GenBank Accession No. AF106324, *Arabidopsis thaliana* sodium proton exchanger Nhx1 mRNA, partial cds, 1999.
GenBank Accession No. AF490589, *Arabidopsis thaliana* $Na^+/H^+$ exchanger 5 (NHX5) mRNA, complete cds, 2002.
GenBank Accession No. AU032554, Rice green shoot *Oryza sativa* (japonica cultivar-group) cDNA clone S10715_12Z, mRNA sequence, 2002.
GenBank Accession No. C91832, Rice panicle shorter than 3cm *Oryza sativa* cDNA clone, 1998.
GenBank Accession No. C91861, Rice panicle shorter than 3cm *Oryza sativa* (japonica cultivar-group) cDNA clone E31967_2A, mRNA sequence, 2002.
GenBank Accession No. CAB10103, *Schizosaccharomyces pombe*, 2003.
GenBank Accession No. L44032, *Hordeum vulgare* (clone ABG494) STS mRNA, sequence tagged site, 1995.
GenBank Accession No. T51330, Human $Na^+/H^+$ exchanger isoform NHE3 composite cDNA, 1997.
GenBank Accession No. T75860, Lambda-PRL2 *Arabidopsis thaliana* cDNA clone 147H20T7, mRNA sequence, 1998.
GenBank Accession No. AV785096, RAFL6 *Arabidopsis thaliana* cDNA clone, 2002.
GenBank Accession No. AV798305, RAFL9 *Arabidopsis thaliana* cDNA clone, 2002.

Gisbert, C. et al. "The yeast HAL1 gene improves salt tolerance of transgenic tomato" *Plant Physiology*, 2000, 123:393-402.

Gordon-Kamm, W.J. et al. "Transformation of maize cells and regeneration of fertile transgenic plants" *The Plant Cell*, 1990, 2:603-618.

Guo, H.H. et al. "Protein tolerance to random amino acid change" *PNAS*, 2004, 101:9205-9210.

Hahnenberger, K.M. et al. "Functional expression of the *Schizosaccharomyces pombe* $Na^+/H^+$ antiporter gene, sod2, in *Saccharomyces cerevisiae*" *Proc. Natl. Acad. Sci. USA*, 1996, 93:5031-5036.

Hiei, Y. et al. "Efficient Transformation of Rice (*Oryza sativa* L.) mediated by Agrobacterium and sequence analysis of the boundaries of the T-DNA" 1994, 6:271-282.

Hill, M.A. and Preiss, J. "Functional analysis of conserved histidines in ADP-glucose pyrophosphorylase from *Escherichia coli*" *Biochem. Biophys. Res. Comm.*, 1998, 244:573-577.

Ichida, A.M. and Schroeder, J.I. "Increased resistance to extracellular cation block by mutation of the pore domain of the *Arabidopsis* inward-rectifying $K^+$ channel KAT1" *J. Membrane Biol.*, 1996, 151:53-62.

Jacoby, M. "Botanists design plants with a taste for salt" *Chemical Engineering News*, 1999, p. 9.

Kaufman, M. "A new strain of tomatoes, and don't hold the salt" *Washington Post*, Jul. 31, 2001, p. A03.

Kinclova, O. et al. "Functional study of the *Saccharomyces cerevisiae* Nha1p C-terminus" *Mol Microbiol.*, 2001, 40:656-668.

Lazar, E. et al. "Transforming growth factor α: Mutation of aspartic acid 47 and leucine 48 results in different biological activities" *Mol Cell Biol.*, 1988, 8:1247-1252.

Liu, W. et al. "Partial deletion of a loop region in the high affinity $K^+$ transporter HKT1 changes ionic permeability leading to increased salt tolerance" *J. Biol. Chem.*, 275:27924-27932.

Maser, P. et al. "Phylogenetic relationships within cation transporter families of Arabidopsis" *Plant Physiology*, 2001, 126:1646-1667.

Nass, R. and Rao, R. "Novel Localization of a $Na^+/H^+$ Exchanger in a late Endosomal Compartment of Yeast"*J. Biol. Chem.*, 1998, 273:21054-21060.

Nass, R. et al. "Intracellular Sequestration of Sodium by a Novel $Na^+/H^+$ Exchanger in Yeast is Enhanced by Mutations in the Plasma Membrane $H^+$ -ATPase" *J. Biol. Chem.*, 1997, 272:26145-26152.

Numata, M. et al., "Identification of a mitochondrial $Na^+/H^+$ exchanger" *J. Biol. Chem.*, 1998, 273:6951-6959.

O'Conner, A. "Altered tomato thrives in salty soil" *New York Times*, Aug. 14, 2001.

Ohki, R. et al. "Preference of the recombination sites involved in the formation of extrachromosomal copies of the human alphoid Sau3A repeat family" *Nucleic Acids Res.*, 1995, 23:4971-4977.

Ohta, M. et al. "Introduction of a $Na^+/H^+$ antiporter gene from Atriplex gmelini confers salt tolerance to rice" *FEBs Letters*, 2002, 26785:1-4.

Orlowski, J. and Grinstein, S. "$Na^+/H^+$ Exchangers of Mammalian Cells" *J. Biol. Chem.*, 1997, 272:22373-22376.

Plantsp "PlantsP: functional genomics of plant phosphorylation-plantsP protein 27103" Retrieved Feb. 5, 2005 from http://plantsp.sdsc.edu/cgi-bin/detail.cgi?db=plantsp&plantsp_id=27103.

Rausch, T. et al. "Salt stress responses of higher plants: The role of proton pumps and $Na^+/H^+$ -antiporters" *J. Plant Physiol.*, 1996, 148:425-433.

Rhoads, D.M. et al. "Regulation of the Cyanide-Resistant Alternative Oxidase of Plant Mitochondria" *J. Biol. Chem.*, 1998, 273:30750-30756.

Rubio, F. et al. "Genetic selection of mutations in the high affinity $K^+$ transporter HKT1 that define functions of a loop site for reduced $Na^+$ permeability and increased $Na^+$ tolerance" *J. Biol. Chem.*, 1999, 274:6839-6847.

Rus, A.M. et al. "Expressing the yeast HAL1 gene in tomato increased fruit yield and enhances $K^+/Na^+$ selectivity under salt stress" *Plant, Cell and Environ.*, 2001, 24:875-880.

Santa-Maria, G.E. et al. "The HAK1 gene of barley is a member of a large gene family and encodes a high-affinity potassium transporter" *The Plant Cell*, 1997, 9:2281-2289.

Schachtman, D.P. et al. "Molecular and functional characterization of a novel low-affinity cation transporter (LCT1) in higher plants" *Proc. Natl. Acad. Sci. USA*, 1997, 94:11079-11084.

Strathmann, M. et al. "Diversity of the G-protein family: Sequences from five additional α subunits in the mouse" *Proc. Natl. Acad. Sci. USA*, 1989, 86:7407-7409.

Travis, J. "Gene makes tomatoes tolerate salt" *Science News*, 60:68.

Waditee, R. et al. "Halotolerant cyanobacterium *Aphanothece halophytica* contains an $Na^+/H^+$ antiporter, homologous to eukaryotic ones, with novel ion specificity affected by C-terminal tail" *J. Biol. Chem.*, 2001, 276, 36931-36938.

West, D.W. and Taylor, J.A. "Response of six grape cultivars to the combined effects of high salinity and rootzone waterlogging" *J. Amer. Soc. Hort. Sci.*, 1984, 109:844-851.

Zandonella, C. "Gene-modified tomato revels in salty soils" *New Scientist*, retrieved Feb. 23, 2002 from http://www.newscientist.com/channel/health/gm-food/dn1092.

Zhang, H-X. et al. "Engineering salt-tolerant Brassica plants: characterization of yield and see oil quality in transgenic plants with increased vacuolar sodium accumulation" *PNAS*, 2001, 98:12832-12836.

Zhang, H-X. et al. "Transgenic salt-tolerant tomato plants accumulate salt in foliage but not in fruit" *Nature Biotech.*, 2001, 19:765-768.

Sasaki, T. and Yamamoto, K., GenBank Accession No. C91823, "Rice cDNA from panicle" 1997.

Hayakawa, T, et al. "Cloning and Characterization of a $Na^+/H^+$ antiporter gene from the halophyte *Atriplex gmelini*" *Biotechnology Symposium Yokoshu*, Nov. 1998, 16:245-250 (with English abstract).

* cited by examiner

|  | M3 | M4 |
|---|---|---|
| OsNHX1 | FSEDLFFIYLLPPIIFNAGFQVKKKQFFRNFMTITLFGAVGTMISFFTISIAAIAIFSRM |
| NHX1 | FNSSYFFNVLLPPIILNSGYELNQVNFFNNMLSILIFAIPGTFISAVVIGIILYIWTFLG |
| NHE6 | FDPEVFFNILLPPIIFYAGYSLKRRHFFRNLGSILAYAFLGTAISCFVIGSIMYGCVTLM |
| NHE1 | LQSDVFFLFLLPPIILDAGYFLPLRQFTENLGTILIFAVVGTLWNAFFLGGLLYAVCLVG |
| NHE2 | MKTDVFFLYLLPPIVLDAGYFMPTRPFFENLGTIFWYAVVGTLWNSIGIGLSLFGICQIE |
| NHE3 | LTPTLFFFYLLPPIVLDAGYFMPNRLFFGNLGTILLYAVIGTIWNAATTGLSLYGVFLSG |
| NHE4 | MDSSIYFLYLLPPIVLESGYFMPTRPFFENIGSILWWAGLGALINAFGIGLSLYFICQIK |

:* *****:: :*: : * *: :* :. *: . .

B

|  | M5 | M6 |
|---|---|---|
| OsNHX1 | ---NIGTLDVG--QFLAIGAIFSATDSVCTLQVLNQDET-PFLYSLVFGEGVVNDATSIV |
| NHX1 | ----LESIDISFAQAMSVGATLSATDPVTILSIFNAYKVDPKLYTIIFGESLLNDAISIV |
| NHE6 | KVTGQLAGDFYFTQCLLFGAIVSATDPVTVLAIFHELQVDVELYALLFGESVLNDAVAIV |
| NHE1 | ---GEQINNIGLLQTLLFGSIISAVDPVAVLAVFEEIHINELLHILVFGESLLNDAVTVV |
| NHE2 | ---AFGLSDITLLQNLLFGSLISAVDPVAVLAVFENIHVNEQLYILVFGESLLNDAVTVV |
| NHE3 | ---LMGELKIGLLQFLLFGSLIAAVDPVAVLAVFEEVHVNEVLFIIVFGESLLNDAVTVV |
| NHE4 | ---AFGLGDINLLQNLLFGSLISAVDPVAVLAVFEEARVNEQLYMMIFGEALLNDGISVV |

.. : : .*: .:*.*.* * ::. . *. ::*.:: .::*

SODIUM/PROTON ANTIPORTER GENE

CROSS-REFERENCE TO A RELATED APPLICATION

This application is a divisional application of application U.S. Ser. No. 09/888,035, now U.S. Pat. No. 6,861,574; filed Jun. 22, 2001; which is a continuation-in-part of PCT/JP99/07224 filed Dec. 22, 1999; which claims priority to Japanese Application No. 10/365604, filed Dec. 22, 1998.

TECHNICAL FIELD

The present invention relates to a novel $Na^+/H^+$ antiporter derived from plants and the DNA encoding the antiporter, as well as methods for producing and using the same.

BACKGROUND ART

Salt tolerance of plants is important to both agriculture and environmental protection. Today, one third of the land on earth is said to be dry land. Further, it is anticipated that the proportion of dry land will increase in the future, due to the progressive desertification of both cultivated land and green land. Considering the prediction that the world population in the year 2050 will be 1.5 times that of today and the serious problems of provisions arising as a result, development of cultivars that grow on land ill-fitted for cultivation, especially on dry land, as well as cultivation techniques for the same is a matter of great urgency. The problem with agriculture on dry land is salt accumulation. In a dry climate, evapotranspiration outstrips precipitation and continued irrigation on land where much is desired for drainage leads to plenty of salt accumulation, due to the deposition of salt on the surface by acceleration of rise in subterranean water level that bear salinity. Examples where cultivation becomes impossible as a result are known from the ancient past, represented by the end of Tigris-Euphrates civilization. The problem still arises today. Thus, innovation of agriculture, on dry land and on land where salt is accumulated, to enhance the salt tolerance of plants is of great importance (Toshiaki Tanno (1983) *Kagaku to Seibutsu* 21:439-445 "Salt tolerance of crops and mechanism of the same"; Yasutaka Uchiyama (1988) *Kagaku to Seibutsu* 26:650-659 "Agricultural use of salinenvironment").

There are two kinds of stress related to salt stress against plants, namely stress by osmotic pressure and stress by ionicity. An osmotic pressure stress is a stress whose action is the same as the stress by dehydration. It results from high osmotic pressure, due to high salinity environment around the plant, which leads to a setback of water absorption of the plant and at the same time deprivation of water from the plant body. It is known that a mechanism exists in the plant to avoid the osmotic pressure stress. The core substances associated with this function are ions (such as $K^+$, $Na^+$, $Cl^-$, organic acid, etc.) as well as substances called compatible solutes. The term "compatible solute" refers to substances such as sugar, proline (a kind of amino acid), and glycine betaine (a quaternary ammonium compound), and so on, which do not disturb the metabolic pathway or inhibit enzymatic action, even when accumulated at a high concentration in the cell. Plant cells accumulate these substances which, in turn, preserve the osmotic pressure balance to the external world (Manabu Ishitani, Keita Arakawa, and Tetsuko Takabe (1990) *Chemical Regulation of Plants* 25:149-162, "Molecular mechanism of salt tolerance in plants").

Almost no development has been made regarding the mechanism of plants to avoid ionic stress. Absorption of excess $Na^+$ by the plant cell leads to inhibition of intracellular enzyme reaction and finally to metabolic trouble (Toru Matoh (1997) *Chemical Regulation of Plants* 32:198-206, "Salt tolerance mechanism of the plant"). Therefore, it is necessary to eliminate the intracellulary accumulated $Na^+$ from the cell or isolate it into intracellular organs, such as vacuoles. The $Na^+/H^+$ antiporter (sodium/proton antiporter) is assumed to play the central role in this process. The $Na^+/H^+$ antiporters of plant cells are thought to exist on both the cell membrane and the vacuolar membrane. They utilize the pH gradient formed between the biomembranes by the $H^+$ pump ($H^+$-ATPase and $H^+$-PPase), an element that transports $H^+$ as the energy to transport $Na^+$ existing in the cytoplasm out of the cell or into the vacuole. Moreover, it is presumed that plants contacted with salt of high density, have to retain intercellular $K^+/Na^+$ ratio high enough, maintaining the osmotic pressure balance between the cell exterior and interior by accumulating $Na^+$ in the vacuole through the $Na^+/H^+$ antiporter.

The $Na^+/H^+$ antiporters found existing on plasma membrane are well examined in animals, yeasts, bacteria and so on. On the plasma membrane of an animal cell, $H^+$ is carried by the $Na^+/H^+$ antiporter, to maintain the balance of $H^+$ in the cell, utilizing the $Na^+$ concentration gradient between the membranes formed by $Na^+/K^+$-ATPase. Therefore, the antiporter is presumed to be deeply related with intracellular pH modulation, control of the cell volume, as well as $Na^+$ transport through the plasma membrane (Orlowski, J. and Grinstein, S. (1997) *J.Biol.Chem.* 272:22373-22376; Aronson, P. S. (1985) *Ann.Rev.Physiol.* 47:545-560). $Na^+/H^+$ antiporters exist in various cells of animals and six isoforms (NHE 1 to 6) have been reported (Orlowski, J. and Grinstein, S. (1997) *J.Biol.Chem* 272:22373-22376).

The first gene cloned for yeast was the gene (sod2) from fission yeast (*Schizosaccharomyces pombe*), which was cloned as a gene related to $Na^+$ transport and salt tolerance (Jia, Z. P., McCullough, N., Martel, R., Hemmingsen, S. And young, P. G. (1992) *EMBO J.* 11:1631-1640). Also, a gene with high identity to this gene has been found from a budding yeast (*Saccharomyces cerevisiae*), as well as *Zygosaccharomyces rouxii* (named NHA1 and ZSOD2, respectively) (Prior, C. et al. (1996) *FEBS Letter* 387:89-93; Watanabe, Y. et al. (1995) *Yeast* 11:829-838). Two different $Na^+/H^+$ antiporter genes (nhaA, nhaB) have been isolated from *E.coli* (Karpel, R. et al. (1988) *J.Biol.Chem.* 263: 10408-10410; Pinner, E. et al. (1994) *J.Biol.Chem.* 269: 26274-26279), each closely related to $Na^+$ transport and salt tolerance. With respect to plants, activities in algae and such have been examined (Katz, A. et al. (1989) *Biochim.Biophys.Acta* 983:9-14).

On the other hand, there are only reports on activity in plants for antiporters restricted on vacuolar membranes. To date, $Na^+/H^+$ antiporters on the vacuoles have been investigated in connection with salt tolerance in halophytes growing in an environment with high salinity (Matoh, T. et al. (1989) *Plant Physiol.* 89:180-183; Hassidim, M. et al. (1990) Plant Physiol. 94:1795-1801; Barkla, B. J. et al. (1995) *Plant Physiol.* 109:549-556), as well as in glycophytes with high salt tolerance, like barley and sugar beet (Hassidim, M. et al. (1990) 94:1795-1801; Blumwald, E. et al. (1987) *Plant Physiol.* 85:30-33; Garbarino, J. and DuPont, F. M. (1988) *Plant Physiol.* 86:231-236; Garbarino, J. and DuPont, F. M. (1989) *Plant Physiol.* 89:1-4; Staal, M. et al. (1991) *Physiol.Plant.* 82:179-184). The above findings indicate that $Na^+/H^+$ antiporters are closely related to salt tolerance of plants. There are several reports on characteristics of Na$^+$/H$^+$ antiporters on the vacuolar membrane. The Km of the antiporter activity for Na$^+$ is about 10 mM similar to that on cytomembrane of mammals (Blumwald, E. et al. (1987) *Plant Physiol.* 85:30-33; Garbarino, J. and DuPont, F. M. (1988) *Plant Physiol.* 86:231-236; Orlowski, J. (1993) *J.Biol.Chem.* 268:16369-16377). Moreover, it is known that amiloride and amiloride derivatives, which are specific inhibitors of Na$^+$ transporters, inhibit the Na$^+$/H$^+$ antiporters on the plant vacuolar membrane and that on the mammalian plasma membrane in a competitive manner (Blumwald, E. et al. (1987) *Plant Physiol.* 85:30-33; Orlowski, J. (1993) *J.Biol.Chem.* 268:16369-16377; Tse, C. M. et al. (1993) *J.Biol.Chem.* 268:11917-11924; Fukuda, A. et al. (1998) *Plant Cell Physiol.* 39:196-201). These findings suggest the characteristic similarities between Na$^+$/H$^+$ antiporter on the vacuolar membrane of plants and that on mammalian plasma membrane. There are various reports on Na$^+$/H$^+$ antiporter activity of plants as mentioned above, however, in spite of the various trials done, analysis of the substantial part, namely genes as well as proteins thereof, were still left behind (Katz, A. et al. (1989) *Biochim.Biophys.Acta* 983:9-14; Barkla, B. and Blumwald, E. (1991) *Proc.Natl.Acad..Sci.USA* 88:11177-11181; Katz, A., Kleyman, T. R., and Pick, U. (1994) *Biochemistry* 33:2389-2393).

Recently, a gene expected to encode a protein that shares amino acid sequence homology with known Na$^+$/H$^+$ antiporter has been cloned from *Arabidopsis*; however, the function of this gene remains to be resolved (M. P. Apse et al. (1998) Final Programme and Book of Abstracts "11th International Workshop on Plant Membrane Biology", Springer; C. P. Darley et al. (1998) Final Programme and Book of Abstracts "11th International Workshop on Plant Membrane Biology", Springer).

Examples of Na$^+$/H$^+$ antiporter genes isolated from plants are only those isolated from *Arabidopsis*, a dicotyledon, described above. No isolation of genes from monocotyledoneae, including species such as rice and maize, which are industrially useful crops, have been reported until now.

DISCLOSURE OF THE INVENTION

Of all the important crops, rice is a crop with low salt tolerance. Its growth is inhibited to the halves with 150 mM NaCl as compared to barley, which is a highly salt tolerant crop, and shows inhibition of the same level with 250 mM NaCl. Garbarino et al. reported the suppression of Na$^+$ flow to the shoot by accumulating Na$^+$ in the vacuole of the root might increase salt tolerance of barleys (Garbarino, J. and DuPont, F. M. (1988) *Plant Physiol.* 86:231-236). From verifying this fact, it has been known that the Na$^+$/H$^+$ antiporter activity of the barley root vacuolar membrane increases through treatment with salt. It has also been known that barley has far and away a higher activity than rice (Garbarino, J. and DuPont, F. M. (1988) *Plant Physiol.* 86:231-236; Fukuda, A. Yazaki, Y., Ishikawa, T., Koike, S., and Tanaka, Y. (1998) *Plant Cell Physiol.* 39:196-201).

On the contrary, the activity does not rise in rice even if it is treated with salt (Fukuda, A. Yazaki, Y., Ishikawa, T., Koike, S., and Tanaka, Y. (1998) *Plant Cell Physiol.* 39:196-201). Further, Na$^+$ transport from root to the shoot of rice is known to be higher than that of the phragmites, which belong to the Gramineae family, like rice, and shows higher salt tolerance (Matsushita, N. and Matoh, T. (1991) *Physiol.Plant.* 83:170-176). Therefore, it is possible that the strength of Na$^+$/H$^+$ antiporter activity of the root vacuolar membrane is deeply associated with rice salt tolerance. These reports indicate that it might be possible to increase salt tolerance of rice by rising Na$^+$/H$^+$ antiporter activity in the rice root. On this account, there was a desire to isolate genes that might increase Na$^+$/H$^+$ antiporter activity of rice.

This situation led to the present invention, an object of which is to provide an Na$^+$/H$^+$ antiporter derived from monocotyledoneae, preferably rice, and gene(s) encoding the same, as well as a method for producing and using the same. The present invention provides use of the gene for production of salt tolerant plants as a favorable use of the present DNA.

The present inventors identified a cDNA clone from rice anthotaxy that shares homology with the Na$^+$/H$^+$ antiporter (NHX1) gene from the budding yeast by analyzing a base sequence from the GeneBank higher plants database. Using this sequence as a probe, the present inventors succeeded in newly cloning the full-length gene designated "OsNHX1", which is expected to encode the Na$^+$/H$^+$ antiporter of rice.

The isolated OsNHX1 cDNA is approximately 2.3 kb and is presumed to encode a protein of 535 amino acids (FIG. 1). From an amino acid hydrophobicity analysis, the protein was detected to have 12 transmembrane regions (FIG. 2).

The amino acid sequence predicted from OsNHX1 was detected to have significant identity with the amino acid sequence of NHX1 and mammalian Na$^+$/H$^+$ antiporter (NHE)(Table 1). Specifically, high identity was seen in the transmembrane region supposed to be involved in ion transport (FIG. 3).

These three proteins (NHX1 from budding yeast, NHE6 from mammals, and OsNHX1) turned out to form a cluster, according to the dendrogram formed for various Na$^+$/H$^+$ antiporters reported to date (FIG. 4). The OsNHX1 protein of the present invention is expected to be expressed in intracellular organs, such as vacuoles, and play an important role in the Na$^+$ transport of the vacuolar membrane, due to the report that NHX1 protein is expressed in the late endosome (Nass, R. and Rao, R. (1998) *J.Biol.Chem.* 273: 21054-21060) and the indication that NHE6 protein is also expressed in the cell (Numata, M., Petrecca, K., Lake, N. and Orlowski J. (1998) *J.Biol.Chem.* 273:6951-6959).

Further, the present inventors succeeded in obtaining transgenic plants by transferring the isolated OsNHX1 gene into the rice callus and redifferentiating them utilizing *Agrobacterium* method.

The present invention relates to a novel Na$^+$/H$^+$ antiporter derived from monocotyledoneae and the DNA coding said antiporter, as well as methods for production and use, especially for the production of salt tolerant plants using same. More specifically, the present invention provides the following:

(1) a DNA selected from the group consisting of:
  (a) a DNA encoding the protein consisting of the amino acid sequence described in SEQ ID NO: 2, and
  (b) a DNA comprising the coding region of the base sequence described in SEQ ID NO: 1;
(2) a DNA encoding the Na$^+$/H$^+$ antiporter derived from monocotyledoneae selected from the group consisting of:
  (a) a DNA encoding the protein consisting of the amino acid sequence described in SEQ ID NO:2, wherein one or more amino acids are substituted, deleted, inserted and/or added, and
  (b) a DNA hybridizing under a stringent conditions to the DNA consisting of the base sequence described in SEQ ID NO:1;
(3) the DNA of (2), wherein the monocotyledoneae is a plant belonging to the Gramineae family;
(4) a vector comprising the DNA of (1) or (2);

(5) a transformant cell having the DNA of (1) or (2), or the vector of (4);
(6) the transformant cell of (5), wherein the cell is a plant cell;
(7) a protein encoded by the DNA of (1) or (2);
(8) a method for production of the protein of (7), which comprises the steps of:
cultivating the transformant cell of (5), and recovering the expressed protein from said cell or the supernatant of the culture thereof;
(9) a transformant plant comprising the transformant cell of (6);
(10) the transformant plant of (9), wherein the plant is a monocotyledon;
(11) the transformant plant of (10), wherein the plant is a plant belonging to the Gramineae family;
(12) the transformant plant of (11), wherein the plant is rice;
(13) a transformant plant that is the offspring or clone of the transformant plant of any of (9) to (12);
(14) a material for the breeding of the transformant plant of any of (9) to (13);
(15) an antibody that binds to the protein of (7);
(16) a nucleic acid molecule that hybridizes with the DNA described in SEQ ID NO: 1, and which has a chain length of at least 15 nucleotides.

The present invention provides a novel $Na^+/H^+$ antiporter derived from monocotyledoneae, as well as a DNA encoding the same. The base sequence of the cDNA encoding the $Na^+/H^+$ antiporter "OsNHX1", derived from rice and isolated by the present inventors, is indicated in SEQ ID NO: 1. The amino acid sequence of the protein encoded by the cDNA is described in SEQ ID NO: 2.

The "OsNHX1" gene showed significant identity with many known amino acid sequences of the $Na^+/H^+$ antiporters, and especially high identity was observed at sites related to ion transport. This finding suggests that "OsNHX1" protein plays an important role in $Na^+$ transport in rice. It is supposed that $Na^+/H^+$ antiporters of plants are involved in the securement of osmotic pressure balance in the plant body under a high salinity stress. Thus, it is anticipated that the "OsNHX" gene especially can be applied to production of salt tolerant cultivars.

Not only "OsNHX1" protein, but also proteins with equivalent functions, are included in this invention. The term "proteins with equivalent functions to 'OsNHX1' protein" herein means that the object protein functions as an $Na^+/H^+$ antiporter. The activity of an $Na^+/H^+$ antiporter can be detected, for example, by detecting the $H^+$ ejection from the biomembrane vesicle due to addition of $Na^+$ as the recovery of fluorescence, by monitoring $H^+$ concentration gradient between isolated biomembrane vesicle formed by $H^+$-ATPase as the fluorescence extinction of acridine orange (Fukuda, A., Yazaki, Y., Ishikawa, T. Koike, S., and Tanaka, Y. (1998) *Plant Cell Physiol.* 39:196-201).

In one embodiment, the protein with equivalent function to "OsNHX1" is a mutant protein having amino acid sequence with one or more amino acid substitution, deletion, insertion and/or addition to the amino acid sequence of "OsNHX1" protein (SEQ ID NO: 2), and which retains equivalent functions with "OsNHX1" protein. Such proteins can be prepared, for example, according to the following method. A method inducing mutations in the amino acid of "OsNHX1" can be mentioned as one method well known to ordinary skilled in the art. That is, one ordinary skilled in the art can prepare a modified protein with equivalent functions to "OsNHX1" by modifying the amino acid sequence of "OsNHX1" protein (SEQ ID NO: 2). For example, by utilizing a site-directed mutagenesis method (Kramer, W. & Fritz, H.-J. "Oligonucleotide-directed construction of mutagenesis via gapped duplex DNA" *Methods in Enzymology* 154:350-367, 1987) and such with the purpose to increase protein activity or the like. Mutations of amino acids also happen to occur in nature. The protein of this invention include proteins having amino acid sequence with 1 or more amino acids substitution, deletion, insertion or addition to the natural amino acid sequence of "OsNHX1" protein (SEQ ID NO: 2), and that retain equivalent functions to natural proteins, regardless whether they are artificial or derived from nature. There is no limitation on the part or the number of amino acid in the protein to be modified, so long as the modified protein retains equivalent functions with the natural "OsNHX1" protein. Generally, amino acidmodifications are done to amino acids within 100 amino acids, preferably within 50 amino acids, much more preferably within 20 amino acids, and most preferably within 5 amino acids.

In another embodiment, the protein having equivalent functions with "OsNHX1" protein is a protein encoded by a DNA derived from monocotyledoneae that hybridizes to the DNA encoding "OsNHX1" protein (SEQ ID NO: 1), having an equivalent function with "OsNHX1" protein. Techniques such as hybridization techniques (Southern, E. M.: *Journal of Molecular Biology*, Vol.98, 503, 1975) and polymerase chain reaction (PCR) techniques (Saiki, R. K. et al. *Science*, Vol.230, 1350-1354, 1985; Saiki, R. K. et al. *Science*, Vol.239, 487-491, 1988) can be mentioned as techniques known to those skilled in the art for preparing proteins. That is, it is routine for a person skilled in the art to isolate a DNA with high identity to the "OsNHX1" gene from rice or other monocotyledon and obtain proteins with an equivalent function to "OsNHX1" protein from that DNA, using the base sequence of "OsNHX1" gene (SEQ ID NO: 1) or parts thereof as a probe, and oligonucleotides hybridizing specifically to the base sequence of "OsNHX1" gene (SEQ ID NO: 1) as a primer. Such proteins, derived from monocotyledoneae with an equivalent function to the "OsNHX1" protein, obtainable by hybridization technique or PCR technique, are included in the proteins of this invention.

Monocotyledoneae, preferably plants belonging to the Gramineae family can be mentioned as plants used as the source of genes for isolation by hybridization techniques and PCR techniques. For example, besides rice, barley (*Hordeum vulgare*), wheat (*Triticum aestivum*), maize (*Zea mays*) and so on can be mentioned, as plants belonging to the Gramineae family. However, it is not limited to them.

Methods for isolating DNA encoding proteins with an equivalent function to the "OsNHX1" protein using the above-described techniques include, for example, but are not limited to, the following. For example, hybridization of cDNA or genomic libraries, prepared from monocotyledoneae with probes (for example, DNA consisting of the base sequence described in SEQ ID NO: 1 or parts thereof) labeled with $^{32}P$ and such, is carried out. Conditions for hybridization using $^{32}P$ labeled probes are 25° C. (without formamide) as a mild condition and usually 42° C., employing hybridization solutions (50% formamide, 5×SSPE, 2× Denhard's solution, 0.1% (w/v) SDS, and 100 µg/ml of herring sperm DNA (Sambrook J, Fritsch E F, Maniatis T (1989) Molecular cloning: A Laboratory Manual (Cold Spring Harbor Lab., Cold Spring Harbor, N.Y.), $2^{nd}$ Ed.)). Prehybridization is carried out at a minimum for more than an hour, and hybridization is performed for 24 hours. Washing of the hybridized filter is carried out at 25° C. (wash solution: 2×SSC, 0.1% SDS) for a mild condition (a condition with low stringency), at 42° C. (wash solution: 2×SSC, 0.1% SDS) for an ordinary condition, and at 56° C. (wash solution: 0.1×SSC, 0.1% SDS) for a stringent condition (a condition with high stringency).

Partially homologous probes are used to detect cDNA clones that are related, but not identical, to the probe sequences. If neither antibody nor nucleic acid probes are available, a number of alternative strategies can be considered. For example, if the same gene has already been cloned from another species or if a related gene has been cloned from the same species, it would be worthwhile carrying out a series of trial experiments to determine whether there is sufficient conservation of nucleic acid sequence to allow the screening of a cDNA library by hybridization. This is most easily accomplished by performing a series of Southern and northern hybridizations at different stringencies. For example, a large batch (50 µg) of genomic DNA is cleaved with a restriction enzyme that cleaves the probe sequence at one or two well-separated sites. It is a good idea to digest an equal amount of genomic DNA of the original species for use as a positive control. Aliquots (5-10 µg) of the digests are then applied to adjacent slots of a 0.8% agarose gel, electrophoresis is carried out, and the fragments are then transferred to a nitrocellulose filter as described in Chapter 9, pages 9.34-9.41 of Sambrook et al. (1989). The filter is cut into strips, each of which is hybridized under different conditions to identical amounts of radioactive probe. For aqueous hybridization, the ionic strength of the solution is kept constant (usually 1 M $Na^+$) while the temperature of annealing is progressively lowered (from 68° C. to 42° C.). The strips are then washed extensively at the temperature of hybridization with a solution containing 2×SSC, 0.5% SDS. When hybridization is carried out in solvents containing formamide, the temperature and ionic strength are usually kept constant (42° C. and 6×SSC [or 6×SSPE], respectively) while the amount of formamide in the annealing buffer is progressively lowered from 50% to 0%. The strips arc then washed extensively at 50° C. in 6×SSC, 0.5% SDS. A similar series of hybridizations can be carried out with mRNA preparations that have been fractionated by electrophoresis and transferred to a solid support. In both cases, the aim is to establish conditions that will allow the previously cloned gene to be used as a probe for the cDNA of interest, without undue interference from background hybridization.

If the protein encoded by the DNA isolated as above has an equivalent function as "OsNHX1" protein, it generally shows a high amino acid sequence identity with "OsNHX1" protein. The term "high identity" as used herein refers to an identity of at least 60%, or more, preferably 80% or more, more preferably 85% or more, and much more preferably 90% or more. The amino acid sequence identity is calculated, for example, by a homology analysis program (Lipman, D. J. and Pearson, W. R. (1985) *Science* 227, 1435-1441) supplied by GENETYX software (Software development corporation).

The protein of the present invention can be prepared by methods known to those skilled in the art as recombinant proteins or as natural proteins. Recombinant proteins can be prepared, for example, by inserting a DNA encoding the protein of the present invention into an adequate expression vector, transfecting an appropriate cell with the vector and purifying the protein from the transformant cell, as described later on. Alternatively, natural proteins can be prepared, for example, by exposing cell extracts, prepared from cells that express the protein of the present invention (for example, rice cells), to affinity columns to which antibodies, prepared by immunizing appropriate immune animals with prepared recombinant proteins or partial peptides thereof, are attached, and purifying the proteins bound to the column.

Additionally, the present invention provides DNAs encoding the proteins of the present invention described above. The DNAs of the present invention includes genomic DNAs, cDNAs, and chemosynthetic DNAs and so on, and can be any DNA without limitation, so long as it encodes a protein of the present invention. The base sequence of the "OsNHX1" cDNA, included in the present invention, is shown in SEQ ID NO: 1.

The genomic DNA, as well as the cDNA can be prepared according to conventional methods, known to those skilled in the art. Genomic DNA, for example, can be isolated using PCR, by designing appropriate primers from the base sequence information of the gene of the present invention, and then screening a genomic library using the obtained amplified DNA fragment as a probe. Alternatively, for example, it is possible to isolate the cDNA from a cDNA library according to the same manner.

The DNA of the present invention can be, for example, utilized in preparation of recombinant proteins, as well as in production of transformant plants with salt tolerance. In preparing recombinant proteins, generally, a DNA encoding the protein of the present invention is inserted into an appropriate expression vector, the expression vector is transferred into an appropriate cell, the transformed cell is cultivated and the expressed protein is purified.

Recombinant proteins can be prepared, for example, by transferring vectors, having DNAs encoding the protein of the present invention inserted therein, into cells, such as bacterial cells, like *E.coli*, yeast cells, insect cells, mammalian cells, and so on, by known gene transfer methods, like the electroporation method, the calcium phosphate transfection method and such, then expressing the recombinant proteins in the cell. Recombinant proteins expressed in the host cell can be purified according to methods known to those skilled in the art. For example, it is possible to express the protein as a fusion protein, with glutathione S-transferase (GST), using vectors such as pGEX (Pharmacia) in *E.coli*, and purify it using a glutathione column (Shigeo Ohno and Yoshifumi Nishimura (1997) "Cell Engineering supplement: Protocol of protein experiments" Shujun-sha).

Moreover, to prepare transformant plants using the DNA of the present invention, a DNA encoding the protein of the present invention is inserted into an appropriate vector, the vector is transferred into a plant cell, and the obtained transformed plant cell is regenerated. The transfer of the plant expression vector into the plant cell can be done for example, according to the species, through methods utilizing *Agrobacteriums* or methods involving the direct transfer into the cell. Methods that utilize *Agrobacteriums*, for example, are methods of Nagel et al. (*Microbiol.Lett.* 67:325(1990)) and methods of Raineri et al. for rice (*Bio/Technology* 8:33-38(1990)). These are methods in which *Agrobacteriums* are transformed with plant expression vectors (pUC system and so on. For example, pCAMBIA vector (Medical Research Council), etc.), and the transformed *Agrobacteriums* are transferred to plant cells using standard methods, like the leefdisk method, the callus method and so on. Methods for the directly transferring a plant expression vector into a cell include the electroporation method, the particle gun method, the calcium phosphate method, the polyethylene glycol method and so.

There is no limitation on the plant cells to which vectors of the invention may be transferred, but monocotyledonous, preferably plants belonging to the Gramineae family are mentioned. Plants, like maize except rice, can be mentioned as plants belonging to the Gramineae family. Incidentally, the "plant cell" of the present invention includes various forms of plant cells, such as suspension culture cells, protoplasts, a section from the leaf, callus, and so on.

For example, methods, like the callus differentiation method (Kyozuka, J. and Shimamoto, K. (1991) Plant Tissue Culture Manual. Kluwer Academic Publishers, pp B1:1-16; Toki, S. (1997) *Plant Molecular Biology Reporter* 15:16-21), the differentiation method utilizing protoplasts (Shimamoto, K. et al. (1989) *Nature* 338:274-276; Kyozuka, J. et al. (1987) *Mol.Gen.Genet.* 206:408-413), and such in response to the kind of plant used, can be utilized to regenerate transgenic plants from transgenic plant cells to which vectors are introduced.

Transgenic plants produced in this way show high $Na^+/H^+$ antiporter activity as compared to wild-type plants, and are supposed to acquire salt tolerance thereby. Moreover, once a transformed plant transfected with the DNA of the present invention is obtained, it is possible to gain descendants from that plant body by syngenesis or agamogenesis. Alternatively, plants can be mass-produced from breeding materials (for example, seeds, fruits, ears, tubers, tubercles, stubs, callus, protoplast, etc.) obtained from the plant, as well as descendants or clones thereof. Plant cells transferred with the DNA of the present invention, plant bodies including these cells, descendants and clones of the plant, as well as breeding materials obtained from the plant, its descendant and clones, are included in the present invention.

Such high $Na^+/H^+$ antiporter activity as compared to wild-type plants can be achieved either by high expression of $Na^+/H^+$ antiporter (change in quantity) or by expression of $Na^+/H^+$ antiporter with higher activity (change in quality), or may be a result of both.

Further, the present invention provides antibodies binding to the proteins of the present invention described above. Both polyclonal antibodies and monoclonal antibodies are included in the present invention. Preparation of the antibody can be conducted according to methods known to those skilled in the art, for example, using methods of Harlow et al. (Harlow, E. and Lane, D. (1988) Antibodies: A laboratory manual. Cold Spring Harbor Laboratory, Cold Spring Harbor, N.Y.). Polyclonal antibodies can be obtained by injecting fusion proteins, synthesized in *E.coli* or synthesized peptides, into a rabbit as antigens, obtaining rabbit antiserum, and purifying antibodies therefrom by affinity chromatography. Monoclonal antibodies can be obtained by injecting antigens to mouse or rats, cloning and preparing hybridomas, and subjecting thus obtained antibody to affinity chromatography.

Furthermore, the present invention provides nucleic acid molecules that hybridize with the DNA encoding the protein of the present invention, and which have a chain length of at least 15 nucleotides. Such nucleic acid molecules can be used, for example, as probes to detect or isolate the DNA encoding the protein of the present invention, as well as primers to enhance such DNA. Such nucleic acid molecules preferably hybridize specifically to the DNA encoding the protein of the present invention. The term "hybridizes specifically" as used herein means that it hybridizes to the DNA encoding the protein of the present invention but it does not hybridize to DNAs encoding other proteins under a normal hybridization condition, preferably under a stringent condition for hybridization.

In addition, such nucleic acid molecules can be used as antisense oligonucleotides, ribozymes, and soon, that suppress expression of the protein of the present invention. Derivatives and modified forms of the antisense oligonucleotides can be used in the same manner as the antisense oligonucleotide itself. The antisense oligonucleotide does not have to be completely complementary to the nucleotides constituting the given region of the DNA or mRNA, and may include 1 or more nucleotide mismatches, provided it can suppress expression of the protein. An antisense oligonucleotide and a ribozyme that suppresses expression of a protein of the present invention can be a very useful tool for the function analysis of the protein of the present invention.

BRIEF DESCRIPTION OF THE DRAWINGS

FIG. 1 shows the base sequence and the predicted amino acid sequence of the rice $Na^+/H^+$ antiporter (OsNHX1) cDNA. The amino acid sequence is expressed in one letter notation.

FIG. 3 shows the amino acid sequence comparison between OsNHX1 and other $Na^+/H^+$ antiporters. Transmembrane regions (M3 to M6) are indicated above the sequence. Regarding the symbols under amino acids, "*" represents that all amino acids are conserved; ":" and "." represent that amino acid are similar. ":" indicates much more similarity than those indicated by ".". The box with A represents the binding site of the specific inhibitor, amiloride, and the boxes with B represent sites with high identities to the mammalian $Na^+/H^+$ antiporter.

BEST MODE FOR CARRYING OUT THE INVENTION

Any patents, patent applications, and publications cited herein are incorporated by reference.

The present invention will be specifically explained with reference to the following examples. However, it should be noted that the present invention is not limited by these examples.

EXAMPLE 1

Cloning of the Rice Na$^+$/H$^+$ Antiporter Gene

A sequence having identity to Na$^+$/H$^+$ antiporter (NHX1) obtained from budding yeast was analyzed from the database for higher plants of GeneBank. A cDNA clone from the cDNA library of rice panicle was identified. The amino acid sequence predicted from the clone had 37% identity with NHX1. It was presumed that the obtained cDNA clone did not have the full-length base sequence. Therefore, using the cDNA clone as a probe and using the cDNA library constructed from mRNA prepared from the root of rice (*Oryza sativa* L. cv Nipponbare) seedling as the template, selection of a cDNA clone having the full-length insertion was performed.

Rice seeds were imbibed overnight, and placed on cotton mesh suspended over a nutrient solution (0.5 mM NH$_4$H$_2$PO$_4$, 1 mM KNO$_3$, 0.5 mM MgSO$_4$, 12.5 µM Fe-EDTA, 1 mM CaCl$_2$, micronutrients). Cultivation was performed 7 days with a cultivation condition: day(brightness 40 µmol m$^{-2}$ s$^{-1}$) for 14 hours at 30° C., night for 10 hours at 25° C., humidity at 75%.

Poly(A$^+$)RNA from the root of rice seedling was prepared and size fractionated by 5 to 25% sucrose density-gradient by centrifugation. Then, a cDNA library was constructed from the fractions containing relatively large poly(A$^+$)RNAs (Tanaka, Y. et al. (1989) *Plant Physiol.* 90:1403-1407). Double stranded cDNA was synthesized from size fractioned poly(A$^+$)RNA by the method of Gubler and Hoffman (Gubler, U. And Hoffman, B. J. (1983) *Gene* 25:263-269), using oligo dT as the primer. The sample was then size fractioned by high performance liquid chromatography (Tosoh, Tokyo, model CCPD,) using Asahipack GS710 column (Asahi Chemical Industry Co. Ltd., Tokyo; 2.5×50 cm). cDNAs larger than 2 kb were inserted to the EcoRI site of λgt11.

Figure 1:
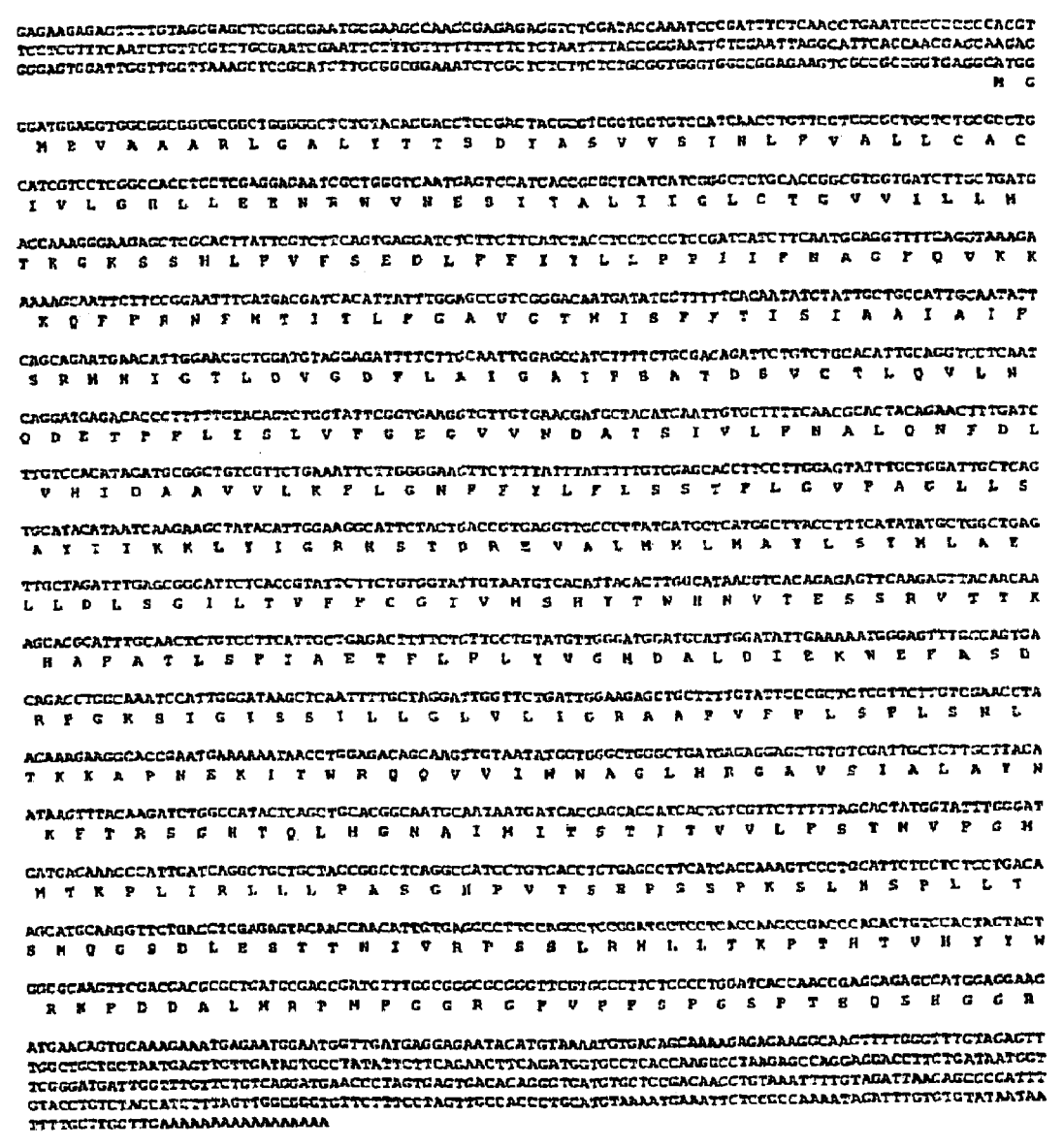

Plaque hybridization was conducted using constructed λ phages having cDNA libraries, and cDNA clones that show identity with the NHX1 as probes. Selecting a vector with the longest cDNA insert from the plaques that showed signal, cloning was performed by inserting the cutout cDNA into a pBluescript(KS+)vector (Stratagene). Confirmation that the obtained cDNA clone is a full-length cDNA was made by the signal size from the Northern hybridization using RNAs extracted from the rice plant body and the obtained clone as the probe. All base sequence of the cDNA, to which the whole isolated gene (referred to as OsNHX1) is inserted, was determined (FIG. 1)

EXAMPLE 2

Base Sequence and Amino Acid Sequence Analysis of OsNHX1 Gene

Figure 2:
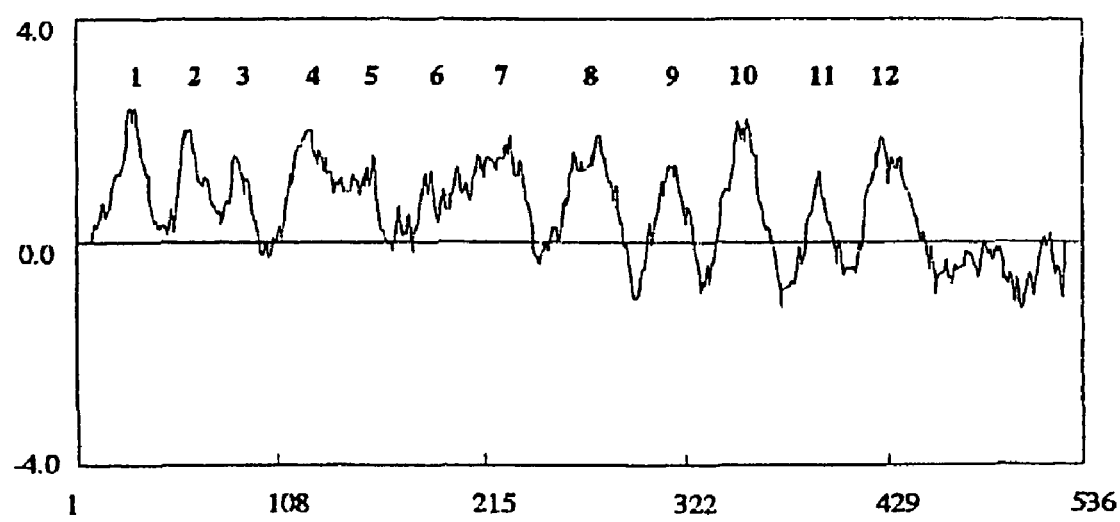
FIG. 2 shows the hydrophobicity plot of the amino acids of the OsNHX1 protein. The abscissa indicates the amino acid residue, and the ordinate indicates the degree of hydrophobicity. Predicted transmembrane regions are shown as boxed numbers.

The full-length sequence was 2330 base pairs, the 5' untranslated region was 296 base pairs, the translated region was 1608 base pairs and the 3' untranslated region was 426 base pairs. The protein encoded by OsNHX1 was predicted to be 535 amino acids long, and the molecular weight was calculated to be 59,070 daltons. 59% of the predicted amino acids sequence was hydrophobic, 22% was neutral amino acids, and 19% was hydrophilic amino acids. Thus, the protein seemed to be highly hydrophobic. The result of hydrophobicity analysis, by the method of Kyte and Doolittle (Kyte, J. And Doolittle, R. F. (1982) *J.Mol.Biol.* 157:105-132), is shown in FIG. 2. Twelve transmembrane regions were detected by the method of TMpred program (Hofmann, K. and Stoffel, W. (1993) *Biol.Chem. Hoppe-Seyler* 374:166).

Significant identity was detected for the amino acid sequence predicted from OsNHX1 with the amino acid sequence of NHX1 and mammalian Na$^+$/H$^+$ antiporter (NHE) (Table 1; NHX1 in the table represents that derived from yeast [S.cerevisiae], NHE6 from human, and NHE1 to 4 from rat. The values on the table were calculated by the homology-analyzing program (Lipman, D. J. and Pearson, W. R. (1985) *Science* 227:1435-1441) of GENETYX (ver.10) software (Software Development Company)). Especially high identity was observed in the transmembrane regions, which were suspected to be involved in ion transport (FIG. 3). $^{83}$LFFIYLLPPI$^{92}$, a part of the amino acid sequence of OsNHX1 (residues 83-92 of SEQ ID NO.2), is very well conserved in NHX1 and NHE and is expected to be the binding site of amiloride, an inhibiter of the eucaryotic Na$^+$/H$^+$ antiporter (Counillon, L. et al. (1993) *Proc.Natl.Acad.Sci.USA* 90:4508-4512) (FIG. 3A). In addition, the 6th and 7th transmembrane regions are well preserved in eucaryotic Na$^+$/H$^+$ antiporter and, thus, is predicted to play an important role in the transport of Na$^+$ and H$^+$ (Orlowski, J. and Grinstein, S. (1997) *J.Biol.Chem.* 272:22373-22376). The 5th and 6th transmembrane regions in the amino acid sequence of OsNHX1 showed high identity to these regions (FIG. 3B). The above results indicate that the protein encoded by OsNHX1 has the activity of Na$^+$/H$^+$ antiporter.

TABLE 1

Amino acid sequence identity of OsNHX1 to other Na$^+$/H$^+$ antiporters (%)

| | OsNHX1 | NHX1 | NHE6 | NHE1 | NHE2 | NHE3 | NHE4 |
|---|---|---|---|---|---|---|---|
| OsNHX1 | 100 | 29.5 | 33.0 | 30.1 | 29.4 | 26.7 | 27.7 |
| NHX1 | | 100 | 36.1 | 28.6 | 29.1 | 29.3 | 32.0 |
| NHE6 | | | 100 | 31.9 | 29.1 | 31.8 | 28.6 |
| NHE1 | | | | 100 | 48.9 | 37.1 | 45.5 |
| NHE2 | | | | | 100 | 44.7 | 66.0 |
| NHE3 | | | | | | 100 | 44.6 |
| NHE4 | | | | | | | 100 |

Figure 4:
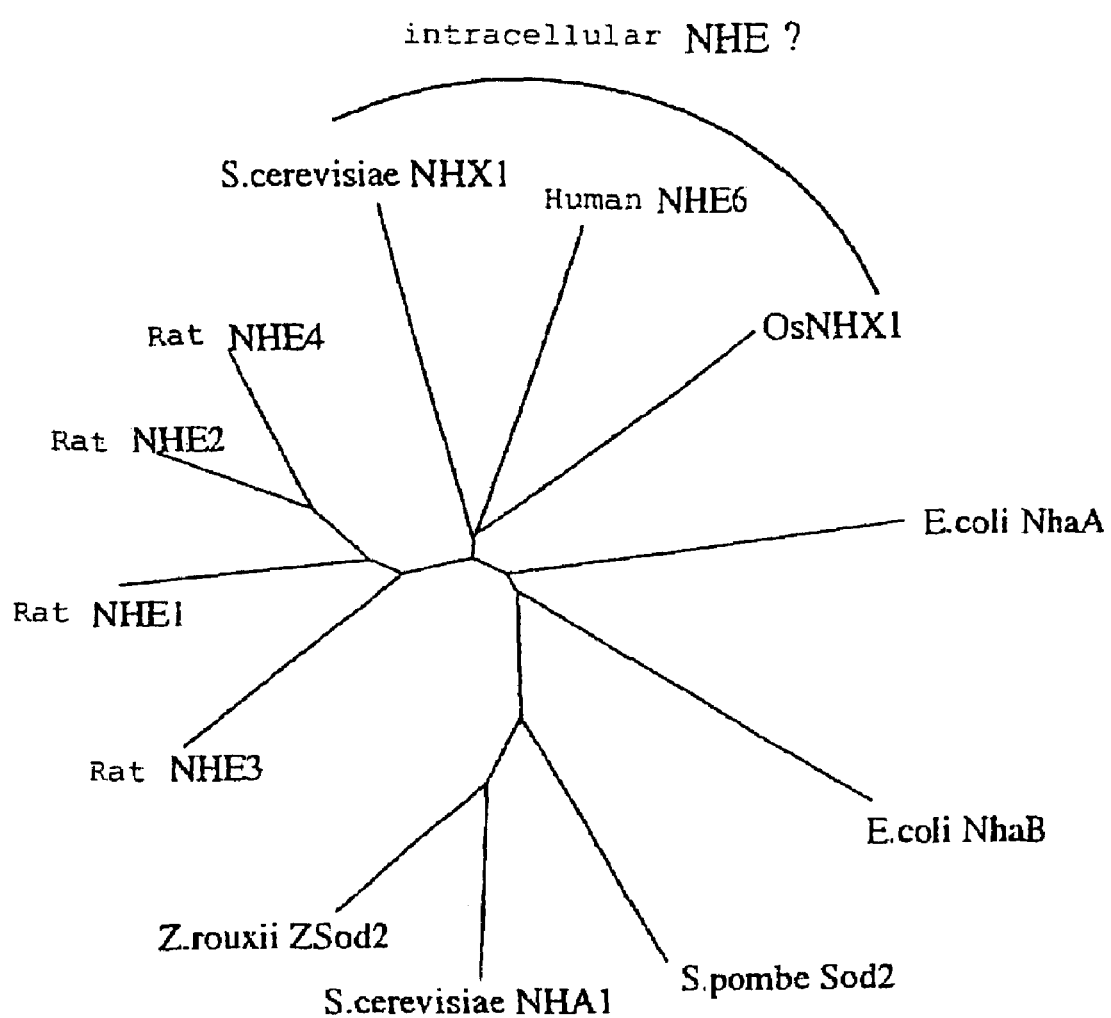
FIG. 4 shows the result of phylogeny analysis of $Na^+/H^+$ antiporter using ClustalX (Thompson, J. D. et al. (1994) *Nucleic Acids Research*, 22:4673-4680) (Neighbor Joining (NJ) method).

Dendrogram of various Na$^+$/H$^+$ antiporters reported to date, namely mammalian NHE, budding yeast (*S. cerevisiae*) NHX1 and NHA1, Sod2 (which is expected to be expressed on the plasma membrane of fission yeast, *S.pombe*), yeast (*Zygosaccharomyces rouxii*) ZSod3, *E. coli* NhaA and NhaB, as well as OsNHX1 (noted as "OsNHX1" in the figures) made according to NJ method, revealed that three of them, that is NHX1, NHE6 and OsNHX1, form a cluster (FIG. 4). It has been reported that NHX1 protein is expressed in the late endosome (Nass, R. and Rao, R. (1998) *J.Biol.Chem.* 273:21054-21060), and it was indicated that NHE6 protein is also expressed in the cell (Numata, M., Petrecca, K., Lake, N. and Orlowski, J., *J.Biol.Chem.* 273: 6951-6959). Therefore, it is expected that OsNHX1 protein is expressed in the intracellular organs, like the vacuole and so on, and plays an important role in Na$^+$ transport in these organs.

EXAMPLE 3

Production of Transformed Rice Expressing Rice Na$^+$/H$^+$ Antiporter Gene

OsNHX1 inserted in the BamHI site of pBluescript KS$^+$ (STRATAGENE) was excised with KpnI and NotI. Then, OsNHX1 was inserted downstream of the cauliflower mosaic virus 35S promoter of pMSH1 (for high expression) and pMSH2 (for repressed expression), both of which are derived from Ti-plasmid and are transferred with kanamycin resistance gene and hygromycine resistance gene (pMSH1: Kawasaki, T. et al. (1999) *Proceedings of the National Academy of Sciences of the U.S.A.* 96:10922-10926; pMSH2: the multi cloning site has the opposite direction compared to pMSH1). Using the constructed vector, the rice callus was transformed with *Agrobacterium tumefaciens*. The callus was induced from the seed, and screened after the infection with *Agrobacterium* was complete using hygromycine. The screened callus was differentiated to obtain the transformant plant. Transformation and differentiation were basically performed according to the method of Toki (Toki, S. (1997) *Plant Molecular Biology* 15,16-21).

EXAMPLE 4

Functional Complementation Experiments in Yeast

Figure 5:
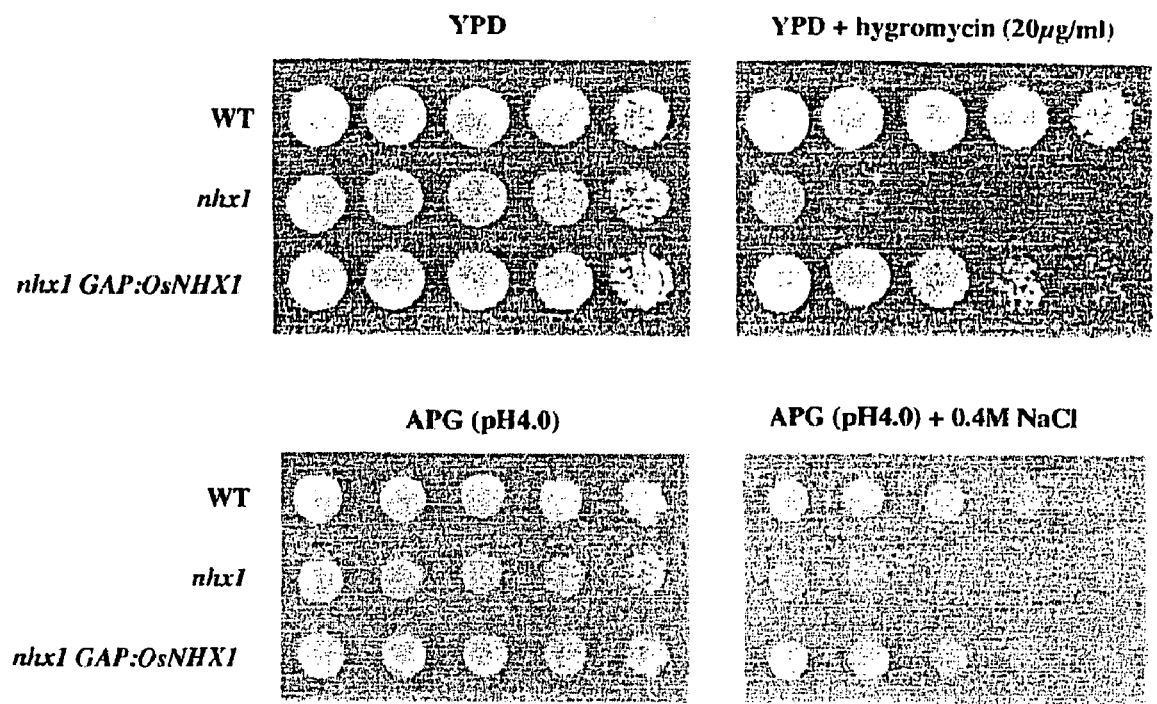
FIG. 5 shows photographs indicating effects of hygromycin and NaCl on budding yeast NHX1 mutant strain (Δnhx1) expressing OsNHX1 gene. WT was K601 (wild-type) containing pKT10 (+HIS3), nhx1 was R100 (Δnhx1) containing pKT10 (+HIS3), and nhx1 GAP:OsNHX1 was R100 containing pKT10 (+HIS3)+OsNHX1. Five-fold serial dilutions (starting at no dilution) of the indicated strains were grown at 28° C. for 3 days on YPD agar medium supplemented with or without hygromycin or for 8 days on APG agar medium (pH 4.0) supplemented with or without NaCl.

Experiments for functional complementation by OsNHX1 gene were performed using budding yeast vacuolar Na$^+$/H$^+$ antiporter gene NHX1 mutant strain (Δnhx1, R100) (Nass, R. et al., (1997) The Journal of Biological Chemistry 272, 26145-26152). Budding yeast was cultured in YPD medium, SD medium, or, in the case of NaCl treatment, APG medium. OsNHX1 gene was inserted downstream of the GAP promoter of pKT10 vector, into which HIS3 gene was inserted. The resulting vector was introduced into budding yeast by lithium method. NaCl- and hygromycin-sensitivity of Δnhx1 was recovered by overexpressing OsNHX1 gene (FIG. 5). Thus, it was confirmed that OsNHX1 gene encoded a protein having vacuolar Na$^+$/H$^+$ antiporter function.

EXAMPLE 5

Localization of OsNHX1 Protein

Figure 6:
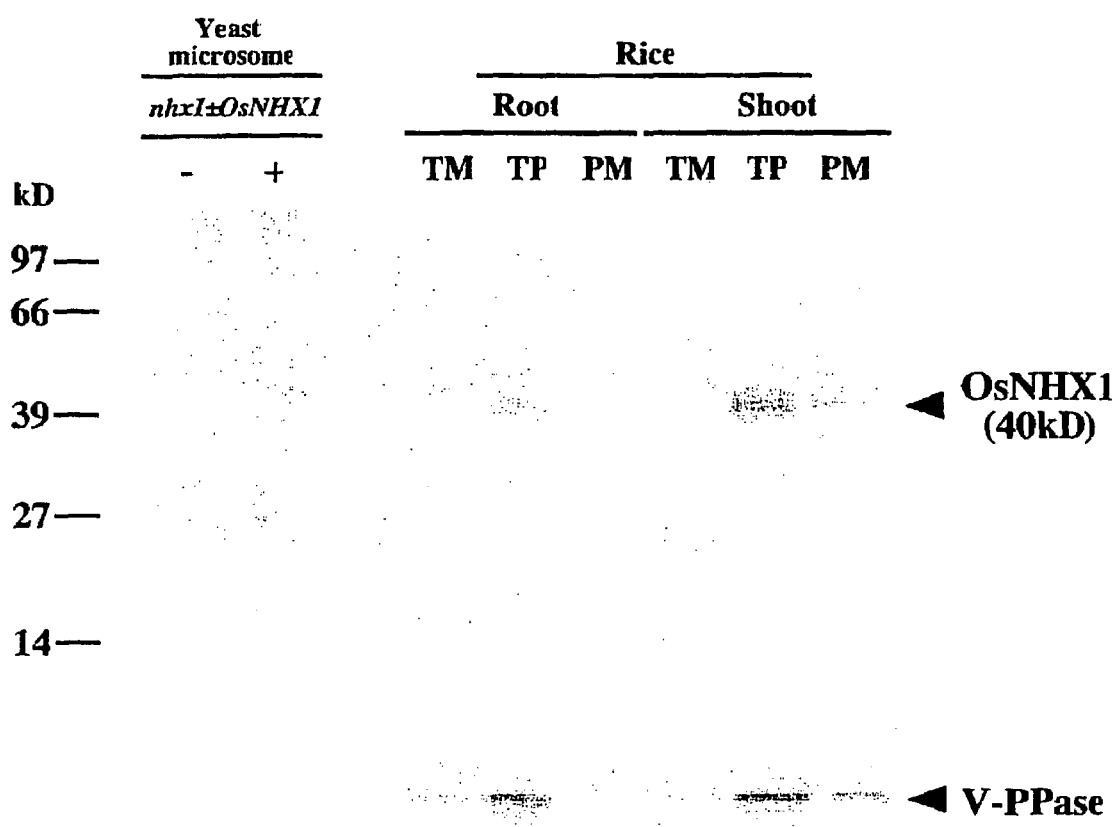
FIG. 6 shows a photograph of electrophoresis indicating results of Western analyses for OsNHX1 protein in a microsomal fraction of budding yeast NHX1 mutant strain (Δnhx1) and a membrane fraction of rice. TM, TP, and PM indicate total membrane, tonoplast, and plasma membrane, respectively. The microsomal fraction of budding yeast was prepared from R100 and R100 into which pKT10 (+HIS3)+OsNHX1 had been introduced. The membrane fraction of rice was prepared from roots and shoots of young rice plants hydroponically cultivated for seven days. The proteins prepared (10 μg) were electrophoresed on a 10% SDS gel and subjected to Western analyses with OsNHX1 protein-specific antibody and vacuolar $H^+$-pyrophosphatase-specific (V-PPase-specific) antibody.

A peptide synthesized on the basis of the carboxyl-terminal 16 amino acids of the amino acid sequence deduced from OsNHX1 gene was injected into a rabbit as an antigen. Antisera obtained were purified by affinity chromatography to prepare OsNHX1 protein-specific polyclonal antibody. Antibody preparation was requested from Sawady Technology Co., LTD. By Western analyses using the OsNHX1 protein-specific antibody obtained, it was confirmed that OsNHX1 protein was largely localized in the tonoplast fraction (FIG. 6). Thus, it was confirmed that OsNHX1 protein was a vacuolar Na$^+$/H$^+$ antiporter.

Industrial Applicability

According to the present invention, it is expected that isolated Na$^+$/H$^+$ antiporter gene can render salt tolerance to the plant by expressing it in the plant. Therefore, it may conduce, for example, an increase in the harvest of crops, due to improvements in salt tolerance, by transfer into useful crops such as rice, which will make them resistant to harm by salt in dry land and such.

We claim:

1. An isolated DNA encoding a protein having an Na+/H+ antiporter activity obtained from a plant wherein said isolated DNA is chosen from:
   (a) a DNA encoding a protein comprising the amino acid sequence described in SEQ ID NO:2;
   (b) a DNA that specifically hybridizes under highly stringent conditions to the DNA consisting of the nucleotide sequence described in SEQ ID NO:1, wherein the highly stringent conditions comprise washing at 65° C. in a wash solution containing 0.1×SSC and 0.1% SDS; or
   (c) a DNA encoding a protein having at least 90% sequence identity to the amino acid sequence described in SEQ ID NO:2.

2. The isolated DNA of claim 1, wherein the plant is a monocotyledonous plant.

3. A vector comprising the isolated DNA of claim 1.

4. A cell transformed with the isolated DNA of claim 1.

5. The transformed cell-from of claim 4, wherein the cell is a plant cell.

6. A transformed plant comprising the transformed plant cell of claim 5.

7. A seed produced by a transformed plant comprising a cell transformed with DNA encoding a protein having an Na+/H+ antiporter activity obtained from a plant wherein said DNA is chosen from:
   (a) a DNA encoding a protein comprising the amino acid sequence described in SEQ ID NO:2;
   (b) a DNA that specifically hybridizes under highly stringent conditions to the DNA consisting of the nucleotide sequence described in SEQ ID NO:1, wherein the highly stringent conditions comprise washing at 65° C. in a wash solution containing 0.1×SSC and 0.1% SDS; or
   (c) a DNA encoding a protein having at least 90% sequence identity to the amino acid sequence described in SEQ ID NO:2.

8. The isolated DNA of claim 2, wherein the monocotyledonous plant is selected from the group consisting of rice, barley, wheat, and maize.

9. The isolated DNA of claim 1, wherein said DNA encodes a protein comprising the amino acid sequence described in SEQ ID NO:2.

10. The isolated DNA of claim 1, wherein said DNA hybridizes under highly stringent conditions to the DNA consisting of the nucleotide sequence described in SEQ ID NO:1, wherein highly stringent conditions comprise washing at 65° C. in a wash solution containing 0.1×SSC and 0.1% SDS.

11. The isolated DNA of claim 1, wherein said DNA encodes a protein having at least 90% sequence identity to the amino acid sequence described in SEQ ID NO:2.

12. The isolated DNA of claim 1, wherein said DNA encodes a protein having at least 95% sequence identity to the amino acid sequence described in SEQ ID NO:2.

* * * * *

UNITED STATES PATENT AND TRADEMARK OFFICE
CERTIFICATE OF CORRECTION

PATENT NO. : 7,326,827 B2 Page 1 of 1
APPLICATION NO. : 10/944174
DATED : February 5, 2008
INVENTOR(S) : Atsunori Fukuda and Yoshiyuki Tanaka It is certified that error appears in the above-identified patent and that said Letters Patent is hereby corrected as shown below:

Title Page,
Item 45, "Date of Patent: Feb. 5, 2008" should read --Date of Patent: *Feb. 5, 2008--.
(Not shown on patent) should read --This patent is subject to a terminal disclaimer.--.

Column 9,
Line 65, "and soon," should read --and so on,--.

Column 21,
Claim 5, "transformed cell-from of claim" should read --transformed cell of claim--.

Signed and Sealed this

Twenty-fourth Day of June, 2008

JON W. DUDAS
*Director of the United States Patent and Trademark Office*

UNITED STATES PATENT AND TRADEMARK OFFICE
CERTIFICATE OF CORRECTION

PATENT NO. : 7,326,827 B2 Page 1 of 1
APPLICATION NO. : 10/944174
DATED : February 5, 2008
INVENTOR(S) : Atsunori Fukuda and Yoshiyuki Tanaka It is certified that error appears in the above-identified patent and that said Letters Patent is hereby corrected as shown below:

Title Page,
Item 45, "Date of Patent: Feb. 5, 2008" should read --Date of Patent: *Feb. 5, 2008--.
(Not shown on patent) should read --This patent is subject to a terminal disclaimer.--.

Column 9,
Line 65, "and soon," should read --and so on,--.

Column 21,
Claim 5, line 43, "transformed cell-from of claim" should read --transformed cell of claim--.

This certificate supersedes the Certificate of Correction issued June 24, 2008.

Signed and Sealed this

Twenty-second Day of July, 2008

JON W. DUDAS
*Director of the United States Patent and Trademark Office*

SEQUENCE LISTING

<160> NUMBER OF SEQ ID NOS: 2

<210> SEQ ID NO 1
<211> LENGTH: 2330
<212> TYPE: DNA
<213> ORGANISM: Oryza sativa
<220> FEATURE:
<221> NAME/KEY: CDS
<222> LOCATION: (297)..(1901)
<223> OTHER INFORMATION:

<400> SEQUENCE: 1

```
gagaagagag ttttgtagcg agctcgcgcg aatgcgaagc caaccgagag aggtctcgat      60
accaaatccc gatttctcaa cctgaatccc cccccacgt tcctcgtttc aatctgttcg     120
tctgcgaatc gaattctttg ttttttttc tctaatttta ccgggaattg tcgaattagg     180
cattcaccaa cgagcaagag gggagtggat tggttggtta aagctccgca tcttgcggcg     240
```

-continued

```
gaaatctcgc tctcttctct gcggtgggtg gccggagaag tcgccgccgg tgaggc atg      299
                                                          Met
                                                           1 ggg atg gag gtg gcg gcg gcg cgg ctg ggg gct ctg tac acg acc tcc        347
Gly Met Glu Val Ala Ala Ala Arg Leu Gly Ala Leu Tyr Thr Thr Ser
         5                  10                  15 gac tac gcg tcg gtg gtg tcc atc aac ctg ttc gtc gcg ctg ctc tgc        395
Asp Tyr Ala Ser Val Val Ser Ile Asn Leu Phe Val Ala Leu Leu Cys
         20                  25                  30 gcc tgc atc gtc ctc ggc cac ctc ctc gag gag aat cgc tgg gtc aat        443
Ala Cys Ile Val Leu Gly His Leu Leu Glu Glu Asn Arg Trp Val Asn
     35                  40                  45 gag tcc atc acc gcg ctc atc atc ggg ctc tgc acc ggc gtg gtg atc        491
Glu Ser Ile Thr Ala Leu Ile Ile Gly Leu Cys Thr Gly Val Val Ile
50                  55                  60                  65 ttg ctg atg acc aaa ggg aag agc tcg cac tta ttc gtc ttc agt gag        539
Leu Leu Met Thr Lys Gly Lys Ser Ser His Leu Phe Val Phe Ser Glu
                 70                  75                  80 gat ctc ttc ttc atc tac ctc ctc cct ccg atc atc ttc aat gca ggt        587
Asp Leu Phe Phe Ile Tyr Leu Leu Pro Pro Ile Ile Phe Asn Ala Gly
                 85                  90                  95 ttt cag gta aag aaa aag caa ttc ttc cgg aat ttc atg acg atc aca        635
Phe Gln Val Lys Lys Lys Gln Phe Phe Arg Asn Phe Met Thr Ile Thr
             100                 105                 110 tta ttt gga gcc gtc ggg aca atg ata tcc ttt ttc aca ata tct att        683
Leu Phe Gly Ala Val Gly Thr Met Ile Ser Phe Phe Thr Ile Ser Ile
         115                 120                 125 gct gcc att gca ata ttc agc aga atg aac att gga acg ctg gat gta        731
Ala Ala Ile Ala Ile Phe Ser Arg Met Asn Ile Gly Thr Leu Asp Val
130                 135                 140                 145 gga gat ttt ctt gca att gga gcc atc ttt tct gcg aca gat tct gtc        779
Gly Asp Phe Leu Ala Ile Gly Ala Ile Phe Ser Ala Thr Asp Ser Val
                 150                 155                 160 tgc aca ttg cag gtc ctc aat cag gat gag aca ccc ttt ttg tac agt        827
Cys Thr Leu Gln Val Leu Asn Gln Asp Glu Thr Pro Phe Leu Tyr Ser
                 165                 170                 175 ctg gta ttc ggt gaa ggt gtt gtg aac gat gct aca tca att gtg ctt        875
Leu Val Phe Gly Glu Gly Val Val Asn Asp Ala Thr Ser Ile Val Leu
             180                 185                 190 ttc aac gca cta cag aac ttt gat ctt gtc cac ata gat gcg gct gtc        923
Phe Asn Ala Leu Gln Asn Phe Asp Leu Val His Ile Asp Ala Ala Val
         195                 200                 205 gtt ctg aaa ttc ttg ggg aac ttc ttt tat tta ttt ttg tcg agc acc        971
Val Leu Lys Phe Leu Gly Asn Phe Phe Tyr Leu Phe Leu Ser Ser Thr
210                 215                 220                 225 ttc ctt gga gta ttt gct gga ttg ctc agt gca tac ata atc aag aag       1019
Phe Leu Gly Val Phe Ala Gly Leu Leu Ser Ala Tyr Ile Ile Lys Lys
                 230                 235                 240 cta tac att gga agg cat tct act gac cgt gag gtt gcc ctt atg atg       1067
Leu Tyr Ile Gly Arg His Ser Thr Asp Arg Glu Val Ala Leu Met Met
             245                 250                 255 ctc atg gct tac ctt tca tat atg ctg gct gag ttg cta gat ttg agc       1115
Leu Met Ala Tyr Leu Ser Tyr Met Leu Ala Glu Leu Leu Asp Leu Ser
         260                 265                 270 ggc att ctc acc gta ttc ttc tgt ggt att gta atg tca cat tac act       1163
Gly Ile Leu Thr Val Phe Phe Cys Gly Ile Val Met Ser His Tyr Thr
275                 280                 285 tgg cat aac gtc aca gag agt tca aga gtt aca aca aag cac gca ttt       1211
Trp His Asn Val Thr Glu Ser Ser Arg Val Thr Thr Lys His Ala Phe
                 290                 295                 300                 305
```

```
gca act ctg tcc ttc att gct gag act ttt ctc ttc ctg tat gtt ggg    1259
Ala Thr Leu Ser Phe Ile Ala Glu Thr Phe Leu Phe Leu Tyr Val Gly
        310                 315                 320 atg gat gca ttg gat att gaa aaa tgg gag ttt gcc agt gac aga cct    1307
Met Asp Ala Leu Asp Ile Glu Lys Trp Glu Phe Ala Ser Asp Arg Pro
325                 330                 335 ggc aaa tcc att ggg ata agc tca att ttg cta gga ttg gtt ctg att    1355
Gly Lys Ser Ile Gly Ile Ser Ser Ile Leu Leu Gly Leu Val Leu Ile
        340                 345                 350 gga aga gct gct ttt gta ttc ccg ctg tcg ttc ttg tcg aac cta aca    1403
Gly Arg Ala Ala Phe Val Phe Pro Leu Ser Phe Leu Ser Asn Leu Thr
    355                 360                 365 aag aag gca ccg aat gaa aaa ata acc tgg aga cag caa gtt gta ata    1451
Lys Lys Ala Pro Asn Glu Lys Ile Thr Trp Arg Gln Gln Val Val Ile
370                 375                 380                 385 tgg tgg gct ggg ctg atg aga gga gct gtg tcg att gct ctt gct tac    1499
Trp Trp Ala Gly Leu Met Arg Gly Ala Val Ser Ile Ala Leu Ala Tyr
                390                 395                 400 aat aag ttt aca aga tct ggc cat act cag ctg cac ggc aat gca ata    1547
Asn Lys Phe Thr Arg Ser Gly His Thr Gln Leu His Gly Asn Ala Ile
            405                 410                 415 atg atc acc agc acc atc act gtc gtt ctt ttt agc act atg gta ttt    1595
Met Ile Thr Ser Thr Ile Thr Val Val Leu Phe Ser Thr Met Val Phe
        420                 425                 430 ggg atg atg aca aag cca ttg atc agg ctg ctg cta ccg gcc tca ggc    1643
Gly Met Met Thr Lys Pro Leu Ile Arg Leu Leu Leu Pro Ala Ser Gly
    435                 440                 445 cat cct gtc acc tct gag cct tca tca cca aag tcc ctg cat tct cct    1691
His Pro Val Thr Ser Glu Pro Ser Ser Pro Lys Ser Leu His Ser Pro
450                 455                 460                 465 ctc ctg aca agc atg caa ggt tct gac ctc gag agt aca acc aac att    1739
Leu Leu Thr Ser Met Gln Gly Ser Asp Leu Glu Ser Thr Thr Asn Ile
                470                 475                 480 gtg agg cct tcc agc ctc cgg atg ctc ctc acc aag ccg acc cac act    1787
Val Arg Pro Ser Ser Leu Arg Met Leu Leu Thr Lys Pro Thr His Thr
            485                 490                 495 gtc cac tac tac tgg cgc aag ttc gac gac gcg ctg atg cga ccg atg    1835
Val His Tyr Tyr Trp Arg Lys Phe Asp Asp Ala Leu Met Arg Pro Met
        500                 505                 510 ttt ggc ggg cgc ggg ttc gtg ccc ttc tcc cct gga tca cca acc gag    1883
Phe Gly Gly Arg Gly Phe Val Pro Phe Ser Pro Gly Ser Pro Thr Glu
    515                 520                 525 cag agc cat gga gga aga tgaacagtgc aaagaaatga gaatggaatg           1931
Gln Ser His Gly Gly Arg
530                 535 gttgatgagg agaatacatg taaaatgtga cagcaaaaga gagaaggcaa gttttgggtt   1991
tgtagagttt ggctgctgct aatgagttgt tgatagtgcc tatattcttc agaacttcag   2051
atggtgcctc accaaggcct aagagccagg aggaccttct gataatggtt cgggatgatt   2111
ggtttgttct gtcaggatga accctagtga gtgacacagg gtgatgtgct ccgacaacct   2171
gtaaattttg tagattaaca gccccatttg tacctgtcta ccatctttag ttggcgggtg   2231
ttctttccta gttgccaccc tgcatgtaaa atgaaattct ccgccaaaat agatttgtgt   2291
gtataataat tttgcttggt tgaaaaaaaa aaaaaaaaa                          2330

<210> SEQ ID NO 2
<211> LENGTH: 535
<212> TYPE: PRT
<213> ORGANISM: Oryza sativa
```

```
<400> SEQUENCE: 2

Met Gly Met Glu Val Ala Ala Arg Leu Gly Ala Leu Tyr Thr Thr
1               5                   10                  15

Ser Asp Tyr Ala Ser Val Val Ser Ile Asn Leu Phe Val Ala Leu Leu
            20                  25                  30

Cys Ala Cys Ile Val Leu Gly His Leu Leu Glu Glu Asn Arg Trp Val
            35                  40                  45

Asn Glu Ser Ile Thr Ala Leu Ile Ile Gly Leu Cys Thr Gly Val Val
        50                  55                  60

Ile Leu Leu Met Thr Lys Gly Lys Ser Ser His Leu Phe Val Phe Ser
65              70                  75                  80

Glu Asp Leu Phe Phe Ile Tyr Leu Leu Pro Pro Ile Ile Phe Asn Ala
                85                  90                  95

Gly Phe Gln Val Lys Lys Lys Gln Phe Phe Arg Asn Phe Met Thr Ile
                100                 105                 110

Thr Leu Phe Gly Ala Val Gly Thr Met Ile Ser Phe Phe Thr Ile Ser
            115                 120                 125

Ile Ala Ala Ile Ala Ile Phe Ser Arg Met Asn Ile Gly Thr Leu Asp
        130                 135                 140

Val Gly Asp Phe Leu Ala Ile Gly Ala Ile Phe Ser Ala Thr Asp Ser
145                 150                 155                 160

Val Cys Thr Leu Gln Val Leu Asn Gln Asp Glu Thr Pro Phe Leu Tyr
                165                 170                 175

Ser Leu Val Phe Gly Glu Gly Val Val Asn Asp Ala Thr Ser Ile Val
            180                 185                 190

Leu Phe Asn Ala Leu Gln Asn Phe Asp Leu Val His Ile Asp Ala Ala
        195                 200                 205

Val Val Leu Lys Phe Leu Gly Asn Phe Phe Tyr Leu Phe Leu Ser Ser
210                 215                 220

Thr Phe Leu Gly Val Phe Ala Gly Leu Leu Ser Ala Tyr Ile Ile Lys
225                 230                 235                 240

Lys Leu Tyr Ile Gly Arg His Ser Thr Asp Arg Glu Val Ala Leu Met
                245                 250                 255

Met Leu Met Ala Tyr Leu Ser Tyr Met Leu Ala Glu Leu Leu Asp Leu
            260                 265                 270

Ser Gly Ile Leu Thr Val Phe Phe Cys Gly Ile Val Met Ser His Tyr
        275                 280                 285

Thr Trp His Asn Val Thr Glu Ser Ser Arg Val Thr Thr Lys His Ala
        290                 295                 300

Phe Ala Thr Leu Ser Phe Ile Ala Glu Thr Phe Leu Phe Leu Tyr Val
305                 310                 315                 320

Gly Met Asp Ala Leu Asp Ile Glu Lys Trp Glu Phe Ala Ser Asp Arg
                325                 330                 335

Pro Gly Lys Ser Ile Gly Ile Ser Ser Ile Leu Leu Gly Leu Val Leu
            340                 345                 350

Ile Gly Arg Ala Ala Phe Val Phe Pro Leu Ser Phe Leu Ser Asn Leu
        355                 360                 365

Thr Lys Lys Ala Pro Asn Glu Lys Ile Thr Trp Arg Gln Gln Val Val
370                 375                 380

Ile Trp Trp Ala Gly Leu Met Arg Gly Ala Val Ser Ile Ala Leu Ala
385                 390                 395                 400

Tyr Asn Lys Phe Thr Arg Ser Gly His Thr Gln Leu His Gly Asn Ala
                405                 410                 415
```

-continued

```
Ile Met Ile Thr Ser Thr Ile Thr Val Val Leu Phe Ser Thr Met Val
            420             425             430

Phe Gly Met Met Thr Lys Pro Leu Ile Arg Leu Leu Leu Pro Ala Ser
        435             440             445

Gly His Pro Val Thr Ser Glu Pro Ser Ser Pro Lys Ser Leu His Ser
    450             455             460

Pro Leu Leu Thr Ser Met Gln Gly Ser Asp Leu Glu Ser Thr Thr Asn
465             470             475             480

Ile Val Arg Pro Ser Ser Leu Arg Met Leu Leu Thr Lys Pro Thr His
                485             490             495

Thr Val His Tyr Tyr Trp Arg Lys Phe Asp Asp Ala Leu Met Arg Pro
            500             505             510

Met Phe Gly Gly Arg Gly Phe Val Pro Phe Ser Pro Gly Ser Pro Thr
        515             520             525

Glu Gln Ser His Gly Gly Arg
    530             535
```